(12) United States Patent
Urvantsau et al.

(10) Patent No.: US 8,372,247 B2
(45) Date of Patent: Feb. 12, 2013

(54) METHOD FOR AUTOMATICALLY DISTILLING LIQUID SPECIMENS AT ATMOSPHERIC PRESSURE IN A STANDARDIZED DISTILLATION APPARATUS

(75) Inventors: Viachaslau Urvantsau, Mondeville (FR); Hervé Cleris, Curcy sur Orne (FR)

(73) Assignee: Instrumentation Scientifique de Laboratoire ISL, Verson (FR)

( * ) Notice: Subject to any disclaimer, the term of this patent is extended or adjusted under 35 U.S.C. 154(b) by 590 days.

(21) Appl. No.: 12/525,969

(22) PCT Filed: Feb. 8, 2008

(86) PCT No.: PCT/FR2008/050192
§ 371 (c)(1),
(2), (4) Date: Sep. 4, 2009

(87) PCT Pub. No.: WO2008/104685
PCT Pub. Date: Sep. 4, 2008

(65) Prior Publication Data
US 2010/0006416 A1    Jan. 14, 2010

(30) Foreign Application Priority Data
Feb. 13, 2007  (FR) ...................... 07 53218

(51) Int. Cl.
*B01D 3/42* (2006.01)
(52) U.S. Cl. .............................. 202/160; 203/2; 73/61.77
(58) Field of Classification Search ................. 73/61.77; 202/160; 203/2; 700/270, 272
See application file for complete search history.

(56) References Cited

U.S. PATENT DOCUMENTS

| | | | |
|---|---|---|---|
| 3,120,119 A * | 2/1964 | Luther | 374/27 |
| 3,239,432 A * | 3/1966 | Rhodes et al. | 202/160 |
| 3,364,731 A | 1/1968 | Hook | |
| 3,737,280 A * | 6/1973 | Cromp | 432/41 |
| 4,250,739 A | 2/1981 | Audeh et al. | |
| 4,528,635 A * | 7/1985 | Juodikis et al. | 700/270 |
| 6,117,309 A * | 9/2000 | Daspit et al. | 208/184 |
| 2003/0037603 A1 * | 2/2003 | Abaev et al. | 73/61.77 |
| 2005/0213633 A1 * | 9/2005 | Burian et al. | 374/27 |

FOREIGN PATENT DOCUMENTS

| | | |
|---|---|---|
| FR | 2410818 A1 | 6/1979 |
| FR | 2815413 A1 | 4/2002 |
| JP | 62113745 * | 5/1987 |

OTHER PUBLICATIONS

English translation of the Written Opinion of the International Searching Authority.
Article—Prediction of ASTM Method D86 Distillation of Gasolines and Naphthas according to the Fugacity-Filmmodel from Gas Chromatographic Detailed Hydocarbon Analysis, Walker Spieksma, AC Analytical Controls, Rotterdam ,the Netherlands, Journal of Chromatographic Science, vol. 36, Sep. 1998.

* cited by examiner

Primary Examiner — Robert A Hopkins
(74) Attorney, Agent, or Firm — Faegre Baker Daniels

(57) ABSTRACT

Method for automatically distilling liquid specimens in a standardized distillation apparatus containing a heater, a distillation flask, a collecting cylinder and control and regulation means, characterized in that: the specimen is introduced into the distillation flask; this flask is positioned in the distillation apparatus; the specimen to be analysed is classified in a group defined by the standard selected; the distillation is started, with the amount of condensate collected in the collecting cylinder, the temperature of the evaporated vapor, the temperature of the liquid specimen present in the flask, together with an operating parameter of the heater, being constantly measured; and the measured values are sent to the control and regulating means that in return control the operating parameter of the heater so as to obtain, directly and automatically, distillation parameters in accordance with a standard.

11 Claims, 4 Drawing Sheets

Sample of diesel fuel

METHOD FOR AUTOMATICALLY DISTILLING LIQUID SPECIMENS AT ATMOSPHERIC PRESSURE IN A STANDARDIZED DISTILLATION APPARATUS

CROSS-REFERENCE TO RELATED APPLICATIONS

This application is a U.S. National Phase Patent Application based on International Application Serial No. PCT/FR2008/050192 filed Feb. 8, 2008, which claims priority from FR 07/53218 filed on Feb. 13, 2007, the disclosures of which are hereby explicitly incorporated by reference herein.

BACKGROUND OF THE INVENTION

1. Field of the Invention

The present invention relates to a method for automatic distillation of liquid samples, in particular samples of petroleum products under atmospheric pressure in a standardised distillation device.

2. Description of the Related Art

It is known that the distillation characteristics of petroleum products are representative of the performance levels of these products and the risks which may be involved for those using them.

The determination of these characteristics is particularly significant in the case of fuels which are intended for the automotive industry or aviation where problems relating to safety are of prime importance.

These characteristics are in particular tables or lines representing the percentage of a sample evaporated in accordance with the temperature during a distillation or the volume of the residue and the losses.

Specialists are able to deduce from these characteristics the behaviour of a specific petroleum product in a specific situation and therefore determine whether or not this product can be safely used, in order to obtain the desired performance levels.

In this context, specialists have stipulated various standards which define very precisely the conditions under which such distillation characteristics must be obtained.

Consequently, in order to provide usable results, the distillations must be implemented with these standards being strictly complied with.

Various automatic distillation devices are currently commercially available and allow the distillation parameters of an unknown sample to be measured, whilst complying with these standards.

These standardised distillation devices generally comprise:
- a heating element,
- a distillation flask whose neck can be closed by means of a fluid-tight stopper which is provided with a thermometer which allows the temperature of the evaporated vapours to be measured, and can be connected to a condenser,
- a collecting cylinder which allows the condensate to be collected and which is provided with means for measuring the quantity of condensate collected in this manner as a function of time, and
- control and regulation means which allow an operating variable of the heating element to be controlled and varied over time, in particular the temperature or the electrical power of this element in order to obtain distillation parameters, in particular distillation rates and/or times for specific volumes in accordance with a predefined standard.

The standards impose in particular, for a specific group of products, parameters such as the time elapsed between the beginning of heating of the sample and obtaining the initial boiling point IBP, that is to say, the time at which the first drop of condensate is observed in the collecting cylinder, or the time elapsed between the IBP and obtaining the 5% distillation point, that is to say, the point at which 5% of the initial volume of the sample has been collected in the collecting cylinder.

These standards also impose the distillation rate between the 5% distillation point and the point at which there is only 5 ml of sample remaining in the distillation flask (that is to say, the volume of evaporated sample or condensate per unit of time during the distillation) or the time elapsed between the point at which there is only 5 ml of sample remaining in the distillation flask and the final boiling point FBP, that is to say, the end of distillation.

Automatic distillation devices which operate in accordance with these standards currently commercially proposed implement a method according to which:
- a predefined quantity of a sample to be analysed is introduced into the distillation flask,
- the distillation flask is positioned on the heating element, it is closed and connected to the condenser,
- the sample to be analysed is classified in a group defined by the standard selected, and
- the distillation of the sample to be analysed is initiated, with constant measurement of the quantity of condensate collected in the collecting cylinder, the temperature of the evaporated vapours, and the operating variable of the heating element, in particular the temperature or the electrical power of this element, and
- the values thus measured are transmitted to the control and regulation means which in turn control the operating variable of the heating element in order to obtain directly and automatically distillation parameters, in particular distillation rates and/or times for specific volumes in accordance with the standard selected.

Such distillation devices have a given number of disadvantages, in particular linked to the inertia between the measuring point of the temperature of the evaporated vapours and the recovery in the collecting cylinder of the condensed vapours for which the temperature has been measured.

However, the main disadvantage of conventional distillation devices is linked to the requirement to carry out different empirical measurements by means of trial and error before the actual distillation operation, that is to say, the determination of the distillation characteristics of an unknown sample.

Such preliminary measurements are particularly long and further have the disadvantage of requiring a significant volume of sample which is not always available; furthermore, these measurements are largely dependent on the skill of the operator.

It is necessary to select beforehand a group in which the unknown sample can be classified among the groups defined by the selected standard, this group imposing a temperature for the beginning of distillation, and to predict the IBP and the point at which there will be only 5% of sample to be analysed remaining in the distillation flask.

The points predicted in this manner must be entered into the device before the distillation in order to allow the control and regulation means to determine different heating thresholds of the sample, which may vary over time, and consequently control the operating variable of the heating element in order to be able to obtain distillation conditions which are within the limits imposed by the selected standard.

These predictions are often found to be imprecise, which forces the operator to carry out a number of tests before being able to obtain distillation conditions which are within the limits imposed by the selected standard which involves a loss of time which may be significant and in particular a loss of sample which may in some cases be available only in limited quantities.

SUMMARY OF THE INVENTION

The object of the present invention is to propose a method for automatic distillation of liquid samples, in particular samples of petroleum products under atmospheric pressure in a standardised distillation device which allows these various constraints to be overcome and allows a distillation to be carried out directly and without any preliminary tests whilst complying with a standard, with only one parameter being entered into the device beforehand, that is to say, the group in which the sample to be analysed is located, from the series of groups defined by the standard selected.

DETAILED DESCRIPTION OF THE DRAWINGS

Figure 1:
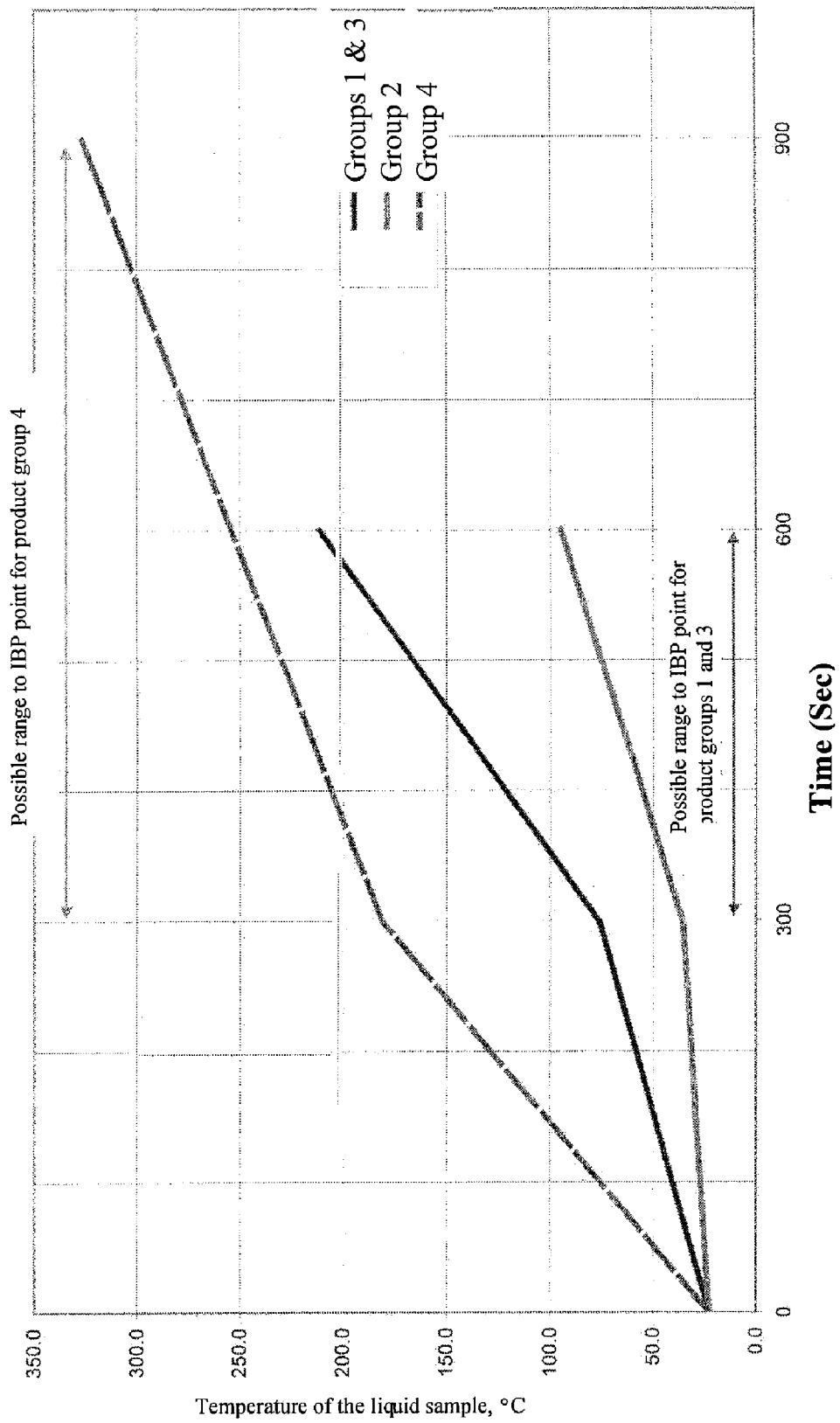
FIG. 1 illustrates the temperature of the liquid in the distillation flask as a function of time.

According to the invention, this method is characterised in that:
  a predefined quantity of a sample to be analysed is introduced into the distillation flask of a standardised distillation device,
  this distillation flask is positioned on the heating element, it is closed and connected to the condenser,
  the sample to be analysed is classified in one of the groups defined by the standard selected, and
  the distillation of the sample to be analysed is initiated, with constant measurement of the quantity of condensate collected in the collecting cylinder, the temperature of the evaporated vapours, the temperature of the liquid sample present in the distillation flask and the operating variable of the heating element, in particular the temperature or the electrical power of this element, and
  the values measured in this manner are transmitted to the control and regulation means which in turn control the operating variable of the heating element in order to obtain directly and automatically characteristics and/or distillation lines in accordance with the standard selected.

According to the invention, the distillation characteristics of the sample to be analysed are the initial boiling point (IBP) and/or the 5% distillation point and/or the point at which there is only 5% of sample to be analysed remaining in the distillation flask.

This method is thus distinguished from the method conventionally implemented when conventional standardised distillation devices are used by the fact that the temperature of the liquid sample present in the distillation flask is constantly measured.

This measurement of the temperature of the liquid sample is generally an indirect measurement; the standards currently in force prevent any direct measurement of this temperature.

The implementation of the method according to the invention allows the standardised distillation device to automatically determine:
  the IBP, the 5% distillation point and the point at which there is only 5% of sample to be analysed remaining in the distillation flask, under conditions imposed by the standard selected,
  the operating variable of the heating element before the IBP and between the IBP and the 5% distillation point in order to obtain these points under the conditions imposed by the standard selected,
  the operating variable of the heating element during distillation between the 5% distillation point and the point at which there is only 5% of sample to be analysed remaining in the distillation flask by automatically correcting this variable in order to obtain a correct distillation rate as imposed by the standard selected, and
  the operating variable of the heating element between the point at which there is only 5% of sample to be analysed remaining in the distillation flask and the final boiling point FBP in order to obtain this point under the conditions imposed by the standard selected.

The method according to the invention further allows the residue in the distillation flask and the losses to be predicted from the distillation characteristics of the sample.

According to a preferred feature of the invention, the temperature of the liquid sample present in the distillation flask is measured indirectly using an infrared sensor.

The use of such a sensor has been found to be particularly advantageous.

According to the invention, the response times of a thermocouple introduced directly into the liquid sample present in the distillation flask and an infrared sensor which allows indirect measurement of the temperature of this sample have thus been compared.

It was thus possible to verify that the use of an infrared sensor allows a sufficiently reliable indication of the temperature of the liquid sample present in the distillation flask to be obtained.

However, in order to be able to viably use such an infrared sensor in order to obtain a correct evaluation of the temperature of the liquid sample present in the distillation flask, it is necessary to block the infrared radiation emitted by the heating element.

According to another feature of the invention, there is interposed to this end, between the heating element and the distillation flask, a perforated insulating plate which is impermeable with respect to infrared radiation.

It is necessary for such a plate to be provided.

In accordance with the invention, the plate may advantageously be produced from a ceramic material based on synthetic compressed calcium silicate, such as, for example, the product marketed by the company ELIT under the name DURATEC 1000.

Taking into account the above, the method according to the invention has the significant advantage of allowing the preliminary prediction of the IBP of an unknown sample to be dispensed with owing to measurements carried out on the sample during the period prior to this point which was previously "omitted".

These measurements allow the IBP to be obtained directly after a heating time corresponding to that imposed by the standard selected following the preliminary introduction into the device of only one item of information, that is to say, the group to which the sample to be analysed belongs according to this standard.

According to a non-limiting feature of the invention, the standard selected is the standard ASTM D 86.

In the specific example of this standard, preliminary tests were carried out according to which sixty-four known products were analysed covering the four groups.

These products were selected in order to obtain the widest possible temperature ranges and distillation gradients for all the characteristic points of the distillation.

Table 1 has thus been set out and indicates the minimum temperature and maximum temperature of the liquid product at the IBP for the products belonging to each of the four groups and the minimum and maximum times which allow this point to be obtained in accordance with the standard.

TABLE 1

| | Minimum | | Maximum | |
|---|---|---|---|---|
| Group | Temperature of the liquid product at IBP | Time between the beginning of heating and the IBP | Temperature of the liquid product at IBP | Time between the beginning of heating and the IBP |
| 1 | 36 | 300 | 95 | 600 |
| 2 | 76 | 300 | 211 | 600 |
| 3 | 36 | 300 | 95 | 600 |
| 4 | 182 | 300 | 327 | 900 |

This table proves by way of example that, for products of group 1 with a low boiling temperature, the temperature of the liquid present in the distillation flask at the IBP is in the order of from 36° C. and is obtained approximately 300 seconds, that is to say, 5 minutes, after the beginning of heating, whilst, for the products of this same group having a high boiling temperature, the temperature of the liquid present in the distillation flask at the IBP is in the order of 95° C. and is obtained approximately 600 seconds, that is to say, 10 minutes, after the beginning of heating.

It is consequently necessary to adjust the variations of the temperature of the liquid sample present in the distillation flask as a function of time in the manner illustrated in FIG. 1.

According to the invention, this adjustment of the temperature of the liquid sample present in the distillation flask was able to be obtained by providing a standardised distillation device with an infrared sensor.

In order to obtain lines which represent the variations of the temperature of the liquid sample present in the distillation flask as a function of time corresponding to that illustrated in FIG. 1, it is necessary to vary an operating variable of the heating element taking into account the dynamic and static properties of this element, that is to say, the variations of temperature and thermal energy losses thereof, in order to control the thermal energy effectively transmitted to the liquid sample present in the distillation flask.

It is considered that a good approximation of this energy is given by the difference existing between the temperature $T_{chauf}$ of the heating element measured continuously by a thermocouple and the temperature $T_{liq}$ of the liquid sample present in the distillation flask measured continuously using the infrared sensor.

It has thus been proposed in accordance with the invention to control the heating of the heating element based on the temperature of the liquid sample present in the distillation flask.

Figure 2:
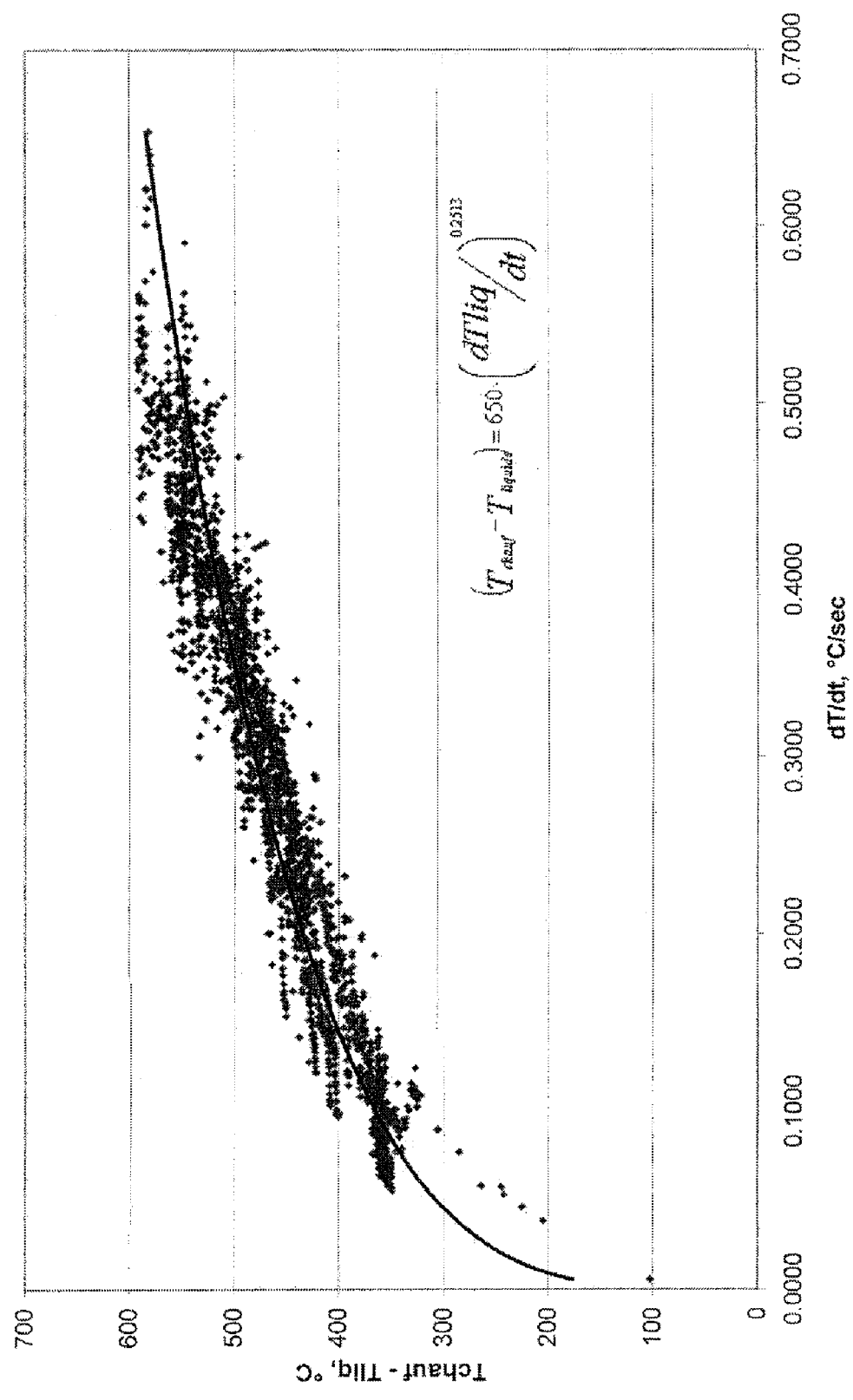
FIG. 2 illustrates the variations of the difference between the temperature $T_{chauf}$ of the heating element and the temperature $T_{liq}$ of the liquid sample in accordance with the variations $dTliq/dt$ of the temperature of this liquid sample as a function of time.

In order to establish the relationship existing between these various control parameters, test products were heated with different heating powers in order to produce the line illustrated in FIG. 2 which represents the variations of the difference between the temperature $T_{chauf}$ of the heating element and the temperature $T_{liq}$ of the liquid sample in accordance with the variations $dTliq/dt$ of the temperature of this liquid sample as a function of time.

It was thus possible to establish that the difference between the temperature $T_{chauf}$ of the heating element and the temperature $T_{liq}$ of the liquid sample present in the distillation flask in accordance with the variations $dTliq/dt$ of the temperature of the liquid sample as a function of time was represented by the equation 1 below:

$$T_{chauf} - T_{liq} = A \cdot (T_{liq}/dt)^2 \quad (I)$$

where A and B are empirical coefficients.

In the specific case of the heating element used, these coefficients had the following values: A=650 and B=0.2513.

Consequently, and according to another feature of the invention, in accordance with the standard ASTM D 86, before the IBP, the temperature $T_{chauf}$ of the heating element is adjusted based on the temperature $T_{liq}$ of the liquid sample present in the distillation flask in accordance with the formula $$T_{chauf} - T_{liq} = A \cdot (T_{liq}/dt)^B$$

where $dTliq/dt$ represent the variations of the temperature of the liquid sample as a function of time provided by the lines in FIG. 1.

The use of this formula allows the adjustment of the temperature of the heating element to be carried out at the beginning of the distillation, before the IBP, in accordance with the standard ASTM D 86 and with minimum error.

However, it was possible to establish, from distillation tests carried out on samples of commercial products such as petrol, diesel, kerosene, that although the implementation of an adjustment of the heating element using the formula I allows a correct IBP to be obtained in accordance with the standard, it does not allow a correct 5% distillation point to be obtained.

It has been found that, in this instance, the thermal energy transmitted to the liquid sample is notably excessively high, this difference being greater for products which are pure or almost pure.

Consequently, it has been considered that the final adjustment in accordance with the formula I preferably had to be carried out before the IBP was reached, that is to say, several seconds before obtaining the first drop of condensate in the collecting cylinder, which involves determining the beginning of the boiling process of the liquid sample present in the distillation flask.

In accordance with the invention, it has been proposed to this end to take into account the abrupt variation of the temperature measured by the vapour thermometer with which the distillation flask is provided.

In order to verify the validity of such a consideration, there have been drawn, on the one hand, for a sample of diesel fuel and, on the other hand, for a petrol, lines representing the variations as a function of time:
   of the temperature of the evaporated vapours measured by the vapour thermometer, the temperature of the liquid sample present in the distillation flask measured by the infrared sensor, variations as a function of time of the temperature of the vapours measured by the vapour thermometer dTvap/dt, and the IBP has been illustrated on these lines.

Figure 3:
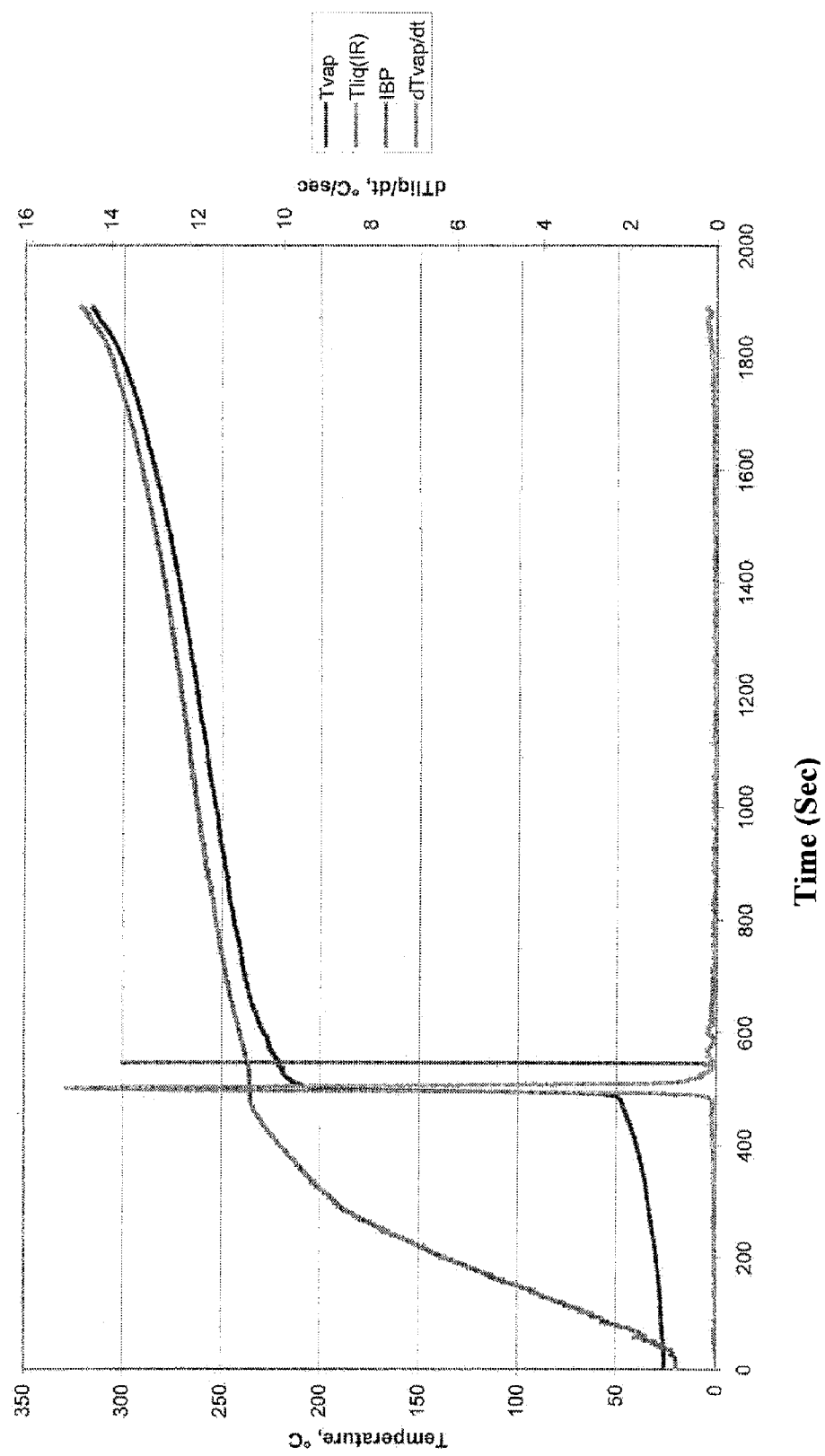
FIG. 3 illustrates the temperature of the evaporated vapours, the temperature of the liquid sample, and variations of the temperature of the vapours as a function of time for a sample of diesel fuel.
Figure 4:
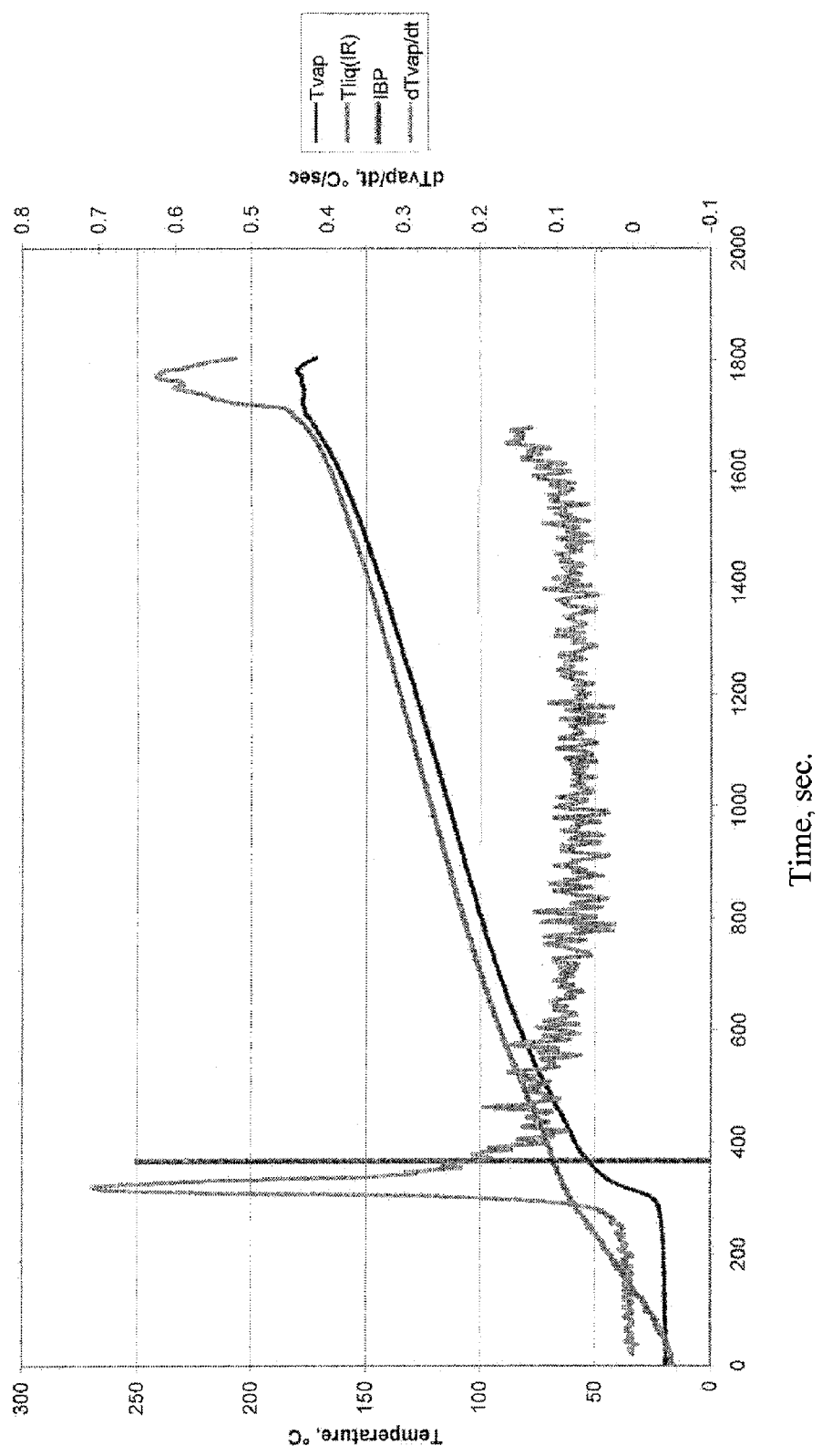
FIG. 4 illustrates the temperature of the evaporated vapours, the temperature of the liquid sample, and variations of the temperature of the vapours as a function of time for a sample of petrol.

These lines are set out in FIGS. 3 and 4, respectively.

These lines show that the observation of the peak representing the variations of dTvap/dt as a function of time allows correct determination of the beginning of the boiling process in the liquid sample present in the distillation flask approximately from 20 to 30 seconds before the IBP.

The method according to the invention thus allows the time to be determined at which the final adjustment must be carried out in accordance with the formula I.

From this final adjustment, the method according to the invention also allows the adjustment to be carried out for the temperature $T_{chauf}$ of the heating element from the temperature $T_{liq}$ of the liquid sample present in the distillation flask measured by the infrared sensor and the temperature $T_{vap}$ of the evaporated vapours measured by the vapour thermometer in order to obtain a correct 5% distillation point under the conditions imposed by the standard ASTM D 86.

According to another feature of the invention, it was possible to establish that this adjustment could be implemented in a satisfactory manner in accordance with the formula II below:

$$(T_{chauf} - T_{liq}) = A0 + A1 \cdot \exp(A2 \cdot T_{liq}) + A3(T_{liq} - T_{vap}) \quad \text{II}$$

where A0, A1, A2 and A3 are empirical coefficients.

In the specific case of the heating element used, these coefficients had the following values: $A0=243.3$, $A1=32.87$, $A2=6.796^e\text{-}3$ and $A3=0.53229$.

The difference $T_{chauf} - T_{liq}$ which substantially corresponds to the energy effectively transmitted to the liquid sample present in the distillation flask can be calculated from two values, that is to say:

- on the one hand, the temperature of the liquid sample measured by the infrared sensor, and
- on the other hand, the difference between the temperature of the liquid sample measured by the infrared sensor and the temperature of the evaporated vapours measured by the vapour thermometer.

The adjustment of the temperature $T_{chauf}$ of the heating element according to the formula II can be carried out from the time at which the evaporated vapours begin to rise in the column of the distillation flask.

This adjustment can be repeated every 1 to 2 seconds taking into account the rapid modifications of the temperature $T_{liq}$ of the liquid sample present in the distillation flask and the temperature $T_{vap}$ of the evaporated vapours.

The adjustment according to the formula II can be stopped after 2 to 3 ml of sample have been recovered in the collecting cylinder and it is then possible to apply the usual algorithm for the adjustment.

According to another feature of the invention, the time is determined, by means of calculation, at which there is only 5% of the sample to be analysed remaining in the distillation flask taking into account the losses and the volume of residue predicted at the end of the distillation, and the temperature $T_{chauf}$ of the heating element is adjusted between the time determined in this manner and the final boiling point (FBP).

From tests carried out on samples of commercial products it was possible to establish that, in order to comply with the requirements of the standard ASTM D86, it was found to be necessary to carry out a final adjustment of the regulation of the temperature of the heating element from the time at which there is only 5 ml of the sample to be analysed remaining in the distillation flask.

Depending on circumstances, from this time, the thermal energy transmitted to the liquid sample can be kept at the previous value thereof or must be slightly reduced or increased.

This requirement is connected to any rapid modifications of the dynamic of the distillation at the end thereof which may bring about abrupt variations of the temperature and an increase of the energy required to heat and evaporate the liquid sample which is still present in the distillation flask.

The variations required for the thermal energy transmitted to the liquid sample are a function of the distillation gradient for the last 5 ml of sample and the type of sample as set out in the table below:

| Gradient ($\Delta c/\Delta v$) for the last 5 ml of sample | Type of sample | Adjustment required for the heating of the sample |
|---|---|---|
| Similar to the mean gradient for the sample | Pure and almost pure compounds, product of the type ether, narrow cut naphtha, solvents, etc . . . | The heating may be slightly reduced in order to obtain a reliable end of the distillation line in order to determine the FBP |
| Slightly greater than the mean gradient of the sample | Direct distillation cuts and the majority of conventional commercial products | The heating may be stabilised at the level of the final value thereof |
| Clearly higher than the mean gradient of the sample | Commercial products contaminated by compounds having a high boiling point, some products following secondary refinement | The heating must be further increased as the gradient becomes greater than the mean gradient of the sample |

It is consequently necessary to be able to determine the time at which there is only 5% of sample to be analysed remaining in the distillation flask.

The invention allows such a determination to be carried out owing to the prediction of the volume of residue at the end of distillation and the losses.

According to the invention, distillation tests were carried out in accordance with the standard ASTM D86 on samples of petrol which are contaminated to a greater or lesser extent with diesel fuel and the mean distillation gradients were determined in the evaporation range of from 10 to 90% of the volume of sample, and the distillation gradients at the time at which there is only 5 ml of sample remaining in the distillation flask and the final adjustment required for the thermal energy transmitted to this sample.

The results obtained in this manner are set out in the table below:

| Sample | Second derivative $d^2T/dV^2$ | Adjustment required of the thermal energy |
|---|---|---|
| Non-contaminated petrol | 0.058 | 0 |
| Petrol + 1% Diesel | 0.062 | 0% . . . 25% |
| Petrol + 3% Diesel | 0.292 | 25% . . . 50% |

-continued

| Sample | Second derivative $d^2T/dV^2$ | Adjustment required of the thermal energy |
|---|---|---|
| Petrol + 7% Diesel | 0.799 | 25% ... 50% |
| Petrol + 15% Diesel | −0.056 | 0% ... 25% |

It was thus possible to establish that the adjustment required for the thermal energy transmitted to the sample at the time where there was only 5 ml of sample remaining in the distillation flask was in correlation with the second derivative $d^2T/dV^2$ of the distillation lines shortly before this time.

During the distillation tests mentioned above, it was in particular possible to establish that the line representing the variations of $d^2T/dV^2$ at the time at which 92% of the sample had been evaporated in accordance with the percentage of contamination of this sample with diesel fuel had a maximum level of between 3 and 10% of contamination corresponding to the range for which the adjustment required for the thermal energy was at a maximum.

This result is capable of proving that the second derivative of the distillation lines can be used in order to predict the final adjustment required for the thermal energy transmitted to the sample at the end of distillation and consequently to automatically carry out this adjustment.

According to the invention, in order to predict the volume of residue, it is considered by hypothesis, on the one hand, that, at the time of the final boiling point FBP, there is no longer any liquid remaining in the base of the distillation flask and, on the other hand, the volume of residue is constituted by two portions, that is to say, the volume $V_{Residu}^{Vap}$ of liquid condensed in the flask from the evaporated vapours and the volume $V_{Residu}^{Reflux}$ of liquid which has flowed back on the walls of the flask.

That is to say, the volume $V_{Residu}$ of the residue corresponds to the following total:

$$V_{Residu} = V_{Residu}^{Vap} + V_{Residu}^{Reflux}$$

According to the invention, it has thus been found that the volume $V_{Residu}$ of the residue could be represented by the equation III below:

$$V_{Residu} = \left[\frac{165 \cdot mm \cdot 273}{22.4 \cdot \rho \cdot (273 + T_{FBP}^{Prevu})}\right] + [C \cdot T_{FBP}^{Prevu} + D] \quad (III)$$

where:
165 represents the volume in milliliters of a distillation flask corresponding to the standard ASTM D86, mm represents the mean molecular mass of the final portion of sample evaporated, ρ represents the density of the final portion of sample evaporated, and $T_{FBP}^{Prevu}$ represents the predicted temperature of the final boiling point FBP, C and D are empirical coefficients obtained using the specific features of the distillation flask of the method D86.

The temperature $T_{FBP}^{Prevu}$ can be obtained by means of extrapolation from temperatures $T_{85\%}$ and $T_{90\%}$ for which 85% and 90% of the volume of the sample have been evaporated.

The values of mm and p may be calculated using empirical equations which are well known to the person skilled in the art from the temperature $T_{FBP}^{Prevu}$.

According to the invention, in order to predict the losses, it is considered that, during a distillation implemented in accordance with the standard ASTM D 86, the losses were directly linked to the vapour pressure in accordance with Reid (RVP) by the relationship:

Loss=0.0142 RVP (kPa)

The vapour pressure RVP can be calculated in real time before the completion of the distillation (standard method using the portion already distilled).

The results of experiments have confirmed this correlation.

The invention claimed is:

1. A method for automatic distillation of liquid samples of petroleum products under atmospheric pressure in accordance with ASTM D86, the method comprising the steps of:
    classifying the sample to be analyzed in a group defined by ASTM D86, the classification defining distillation characteristics of the sample to be analyzed including a time to the initial boiling point (IBP) and/or the 5% distillation point and/or the point at which there is only 5% of sample to be analyzed remaining in the distillation flask;
    providing a distillation device, the distillation device comprising:
        a distillation flask having a neck closable by a fluid-tight stopper;
        a heating element;
        a condenser connected to the distillation flask for condensing evaporated vapors;
        a collecting cylinder connected to the condenser for collecting a quantity of condensate condensed by the condenser;
        a thermometer positioned to measure the temperature of evaporated vapors in the distillation flask; and
        a controller which controls an operating variable of the heating element in accordance with the defined distillation characteristics;
    introducing a predefined quantity of the sample to be analyzed into the distillation flask,
    positioning the distillation flask on the heating element, closing the distillation flask, and connecting the distillation flask to the condenser;
    initiating the distillation of the sample to be analyzed;
    constantly measuring the quantity of condensate collected in the collecting cylinder, the temperature of the evaporated vapors, the temperature of the liquid sample present in the distillation flask, and the operating variable of the heating element during the distillation; and
    controlling the operating variable of the heating element with the controller to obtain the distillation characteristics in accordance with ASTM D86;
    wherein, before the IBP, the temperature $T_{chauf}$ of the heating element is adjusted based on the temperature $T_{liq}$ of the liquid sample present in the distillation flask in accordance with the formula:

$$(T_{chauf} - T_{liq}) = A(dTliq/dt)^{0.2513}$$

where dTliq/dt is $$\frac{95°\,C. - 36°\,C.}{600\,sec - 300\,sec}$$

when the liquid sample is a group 1 or group 3 sample according to ASTM D86, $$\frac{211°\,C.-76°\,C.}{600\sec-300\sec}$$

when the liquid sample is a group 2 sample according to ASTM D86, and $$\frac{327°\,C.-182°\,C.}{900\sec-300\sec}$$

when the liquid sample is a group 4 sample according to ASTM D86.

2. The method according to claim 1, wherein between the IBP and the 5% distillation point, the temperature $T_{chauf}$ of the heating element is adjusted based on the temperature $T_{liq}$ of the liquid sample present in the distillation flask and the temperature $T_{vap}$ of the evaporated vapors measured by the vapor thermometer in accordance with the formula:

$$(T_{chauf}-T_{liq})=A0+A1\cdot\exp(A2\cdot T_{liq})+A3\cdot(T_{liq}-T_{vap}).$$

3. The method according to claim 2, wherein the time for which there is only 5% of the sample remains in the distillation flask is determined taking into account a predicted loss volume of the sample during the distillation and a volume of residue predicted at the end of distillation, and the temperature $T_{chauf}$ of the heating element is adjusted between the determined time and the final boiling point (FBP).

4. A method for the automatic distillation of a liquid petroleum product sample under atmospheric pressure complying with standard ASTM D86 or an equivalent related standard, comprising the steps of:
   providing a distillation device, the distillation device comprising:
      a distillation flask having a neck closable by a fluid-tight stopper;
      a condenser connected to the distillation flask for condensing evaporated vapors;
      a collecting cylinder connected to the condenser for collecting a quantity of condensate condensed by the condenser;
      a first thermometer configured to indirectly measure the temperature of a liquid sample present in the distillation flask;
      a second thermometer configured to measure the temperature of evaporated vapors present in the distillation flask;
      a heating element for heating a sample positioned in the distillation flask; and
      a controller in communication with the first and second thermometers, the controller controlling the heating element;
   classifying the sample in a group, where the group defines distillation parameters including i) a time elapsed between a beginning of the heating and an initial boiling point (IBP), ii) a time between an initial boiling point (IBP) and a 5% distillation point, and iii) a time between a 5% distillation point and a point for which only 5% of the sample remains in the distillation flask;
   introducing a predefined quantify of the sample into the distillation flask;
   closing the fluid-tight stopper and connecting the distillation flask to the condenser;
   heating the distillation flask with the heating element to distill the sample in accordance with the distillation parameters;
   measuring the quantity of condensate collected in the collecting cylinder during the heating step;
   measuring with the first thermometer the temperature of a liquid sample present in the distillation flask and measuring with the second thermometer the temperature of evaporated vapors present in the distillation flask; and
   adjusting, using the controller, the heating rate of the heating element based on i) the temperature of the liquid sample present in the distillation flask at temperatures before the IBP, ii) the temperature of the liquid sample present in the distillation flask and the temperature of the evaporated vapors between the IBP and the 5% distillation point, and iii) the temperature of the evaporated vapors after the 5% distillation point.

5. The method according to claim 4, wherein the temperature of the liquid sample present in the distillation flask is measured using an infrared sensor.

6. The method according to claim 5, wherein a perforated insulating plate which is impermeable with respect to infrared radiation is positioned between the heating element and the distillation flask.

7. The method according to claim 6, wherein the insulating plate which is impermeable with respect to infrared radiation is produced from a ceramic material based on synthetic compressed calcium silicate.

8. The method according to claim 4, characterized in that the standard is the standard ASTM D 86.

9. The method according to claim 4, wherein before the IBP, the temperature $T_{chauf}$ of the heating element is adjusted based on the temperature $T_{liq}$ of the liquid sample present in the distillation flask in accordance with the formula:

$$T_{chauf}-T_{liq}=A(dT\text{liq}/dt)^{0.2513}$$

where $dT\text{liq}/dt$ is $$\frac{95°\,C.-36°\,C.}{600\sec-300\sec}$$

when the liquid sample is a group 1 or group 3 sample according to ASTM D86, $$\frac{211°\,C.-76°\,C.}{600\sec-300\sec}$$

when the liquid sample is a group 2 sample according to ASTM D86, and $$\frac{327°\,C.-182°\,C.}{900\sec-300\sec}$$

when the liquid sample is a group 4 sample according to ASTM D86.

10. The method according to claim 4, wherein between the IBP and the 5% distillation point, the temperature $T_{chauf}$ of the heating element is adjusted based on the temperature $T_{liq}$ of the liquid sample present in the distillation flask and the temperature $T_{vap}$ of the evaporated vapors measured by the vapor thermometer in accordance with the formula:

$$(T_{chauf}-T_{liq})=A0+A1 \cdot \exp(A2 \cdot T_{liq})+A3 \cdot (T_{liq}-T_{vap}).$$

11. The method according to claim 10, wherein the time for which there is only 5% of the sample remains in the distillation flask is determined taking into account a predicted loss volume of the sample during the distillation and a volume of residue predicted at the end of distillation, and the temperature $T_{chauf}$ of the heating element is adjusted between the determined time and the final boiling point (FBP).

* * * * *